US011355222B2

(12) United States Patent
Jarrett et al.

(10) Patent No.: US 11,355,222 B2
(45) Date of Patent: Jun. 7, 2022

(54) ANALYTICS AT THE POINT OF CARE

(71) Applicant: CERNER INNOVATION, INC., Kansas City, KS (US)

(72) Inventors: Lindsey Gay Jarrett, Kansas City, MO (US); Scott Alan Julius, Olathe, KS (US); Eva Karp, Kansas City, MO (US); Brenton Arnold Greubel, Lee's Summit, MO (US); Lisa McDermott, Kansas City, MO (US); Megan Kathleen Romstad, Kansas City, MO (US)

(73) Assignee: CERNER INNOVATION, INC., North Kansas City, MO (US)

( * ) Notice: Subject to any disclaimer, the term of this patent is extended or adjusted under 35 U.S.C. 154(b) by 628 days.

(21) Appl. No.: 15/726,092

(22) Filed: Oct. 5, 2017

(65) Prior Publication Data
US 2019/0108313 A1 Apr. 11, 2019

(51) Int. Cl.
*G16H 20/00* (2018.01)
*G16H 10/60* (2018.01)
*G16H 50/20* (2018.01)
*G16H 50/50* (2018.01)
*G16H 40/20* (2018.01)
*G16H 40/67* (2018.01)

(52) U.S. Cl.
CPC ............ *G16H 10/60* (2018.01); *G16H 20/00* (2018.01); *G16H 40/20* (2018.01); *G16H 40/67* (2018.01); *G16H 50/20* (2018.01); *G16H 50/50* (2018.01)

(58) Field of Classification Search
CPC .................. G16H 20/00; G06Q 50/22–24
See application file for complete search history.

(56) References Cited

U.S. PATENT DOCUMENTS

| 6,000,828 A * | 12/1999 | Leet | G16H 20/10 |
| | | | 705/2 |
| 7,657,445 B1 * | 2/2010 | Goux | G06Q 10/06 |
| | | | 705/3 |
| 8,694,334 B2 * | 4/2014 | Ryan | G16H 10/60 |
| | | | 705/2 |
| 2002/0184050 A1 * | 12/2002 | Papageorge | G16H 15/00 |
| | | | 705/2 |

(Continued)

OTHER PUBLICATIONS

What is Aggregate Data Definition (Year: NA).*

*Primary Examiner* — John A Pauls
(74) *Attorney, Agent, or Firm* — Shook, Hardy & Bacon L.L.P.

(57) ABSTRACT

Analytics relevant to a particular patient are provided within the clinical decision workflow to provide data-driven decision support. When information is received from an end user device at a workflow service that indicates characteristics of a clinical decision support workflow being managed by the end user device for a patient, data is requested from one or more knowledge systems and electronic health record (EHR) data is requested from one or more EHRs. The data and the EHR data is aggregated within the clinical decision support workflow and a recommendation is provided to a clinician at a point of care via the end user device. For example, the recommendation may reveal that a particular care plan is, according to the aggregated data, the model recommendation.

15 Claims, 7 Drawing Sheets

(56) References Cited

U.S. PATENT DOCUMENTS

| | | | |
|---|---|---|---|
| 2011/0313788 A1* | 12/2011 | Amland | G16H 70/20 |
| | | | 705/3 |
| 2013/0325515 A1* | 12/2013 | Nikolova-Simons | |
| | | | G16H 50/30 |
| | | | 705/3 |
| 2014/0129247 A1* | 5/2014 | Op Den Buijs | G06Q 10/10 |
| | | | 705/2 |
| 2015/0006192 A1* | 1/2015 | Sudharsan | G06N 5/048 |
| | | | 705/2 |
| 2018/0075194 A1* | 3/2018 | Allen | G16H 50/30 |

* cited by examiner

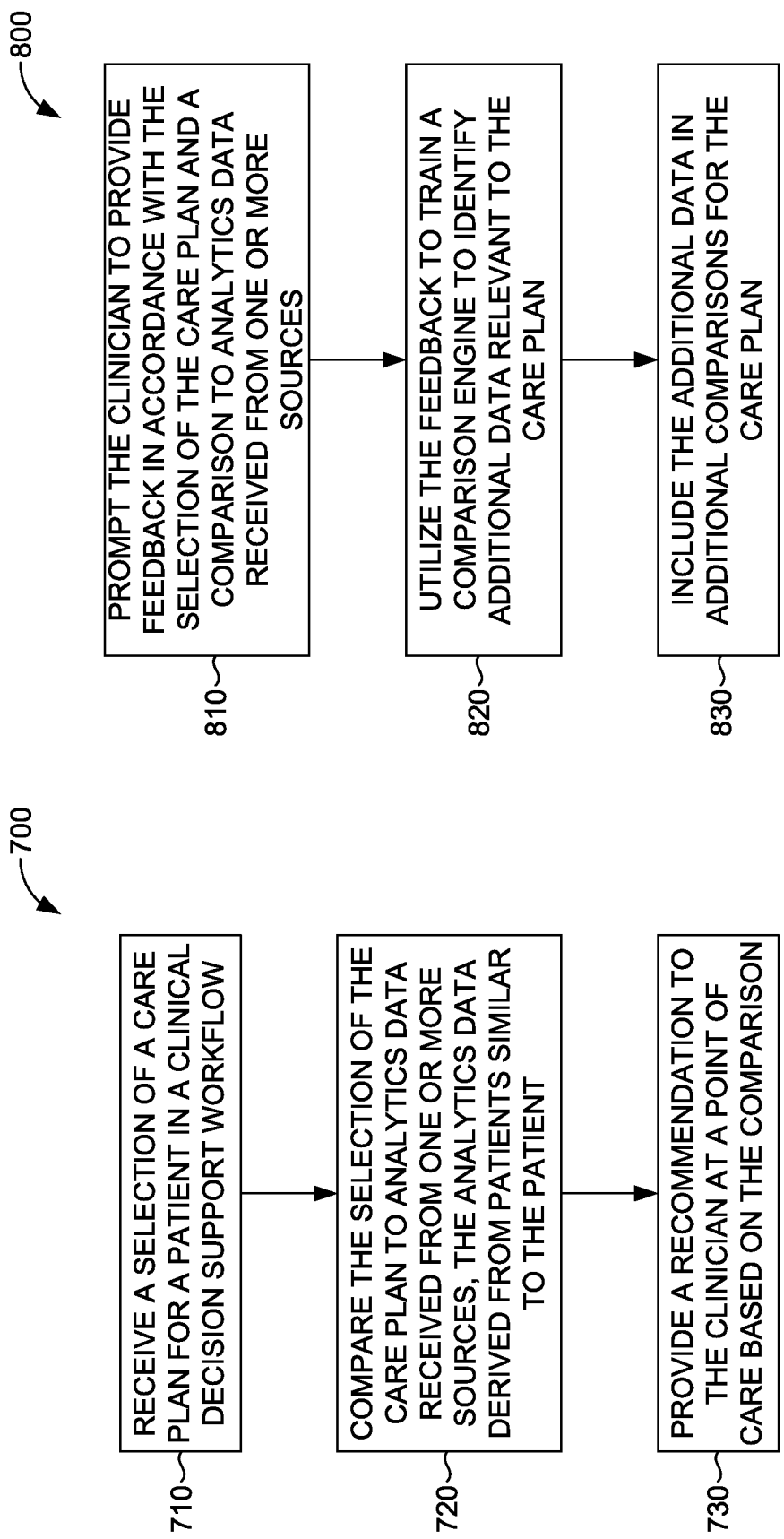

ANALYTICS AT THE POINT OF CARE

BACKGROUND

The modern practice of medicine poses a number of challenges for clinicians to effectively deliver quality care to patients. In particular, the effective medical knowledge base continues to grow at a rapid pace, making it difficult for clinicians to keep up with and carry out recognized best practices. For instance, thousands of new journal articles are published each month providing a plethora of new evidence-based clinical information. Additionally, new drugs, treatment techniques, and testing procedures are continuously being researched and developed. The difficulty for clinicians to keep appraised of such information is exacerbated by the fact that clinicians are typically pulled in many different directions by a vast number of patients. Moreover, clinicians must often make quick decisions regarding patient treatment. Information that is readily available is provided in general terms, without the benefit of analytics. This lack of analytics within the workflow prevents the clinician from weighing evidence-based clinical information within the actual workflow. As a result, there currently exists a gap between evidence-based information and actual clinician practices. This gap contributes to decreased quality of care, increased risk of medical errors, and increased cost of healthcare.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to integrating multi-source data (i.e., analytics) into the clinical decision workflow. More particularly, analytics relevant to a particular patient are provided within the clinical decision workflow to provide data-driven decision support. When information is received from an end user device at a workflow service that indicates characteristics of a clinical decision support workflow being managed by the end user device for a patient, data is requested from one or more knowledge systems and electronic health record (EHR) data is requested from one or more EHRs. The data and the EHR data is aggregated within the clinical decision support workflow and a recommendation is provided to a clinician at a point of care via the end user device. For example, the recommendation may reveal that a particular care plan is, according to the aggregated data, the model recommendation.

BRIEF DESCRIPTION OF THE SEVERAL VIEWS OF THE DRAWINGS

The patent or application file contains at least one drawing executed in color. The present invention is described in detail below with reference to the attached drawing figures, wherein:

Figure 3:
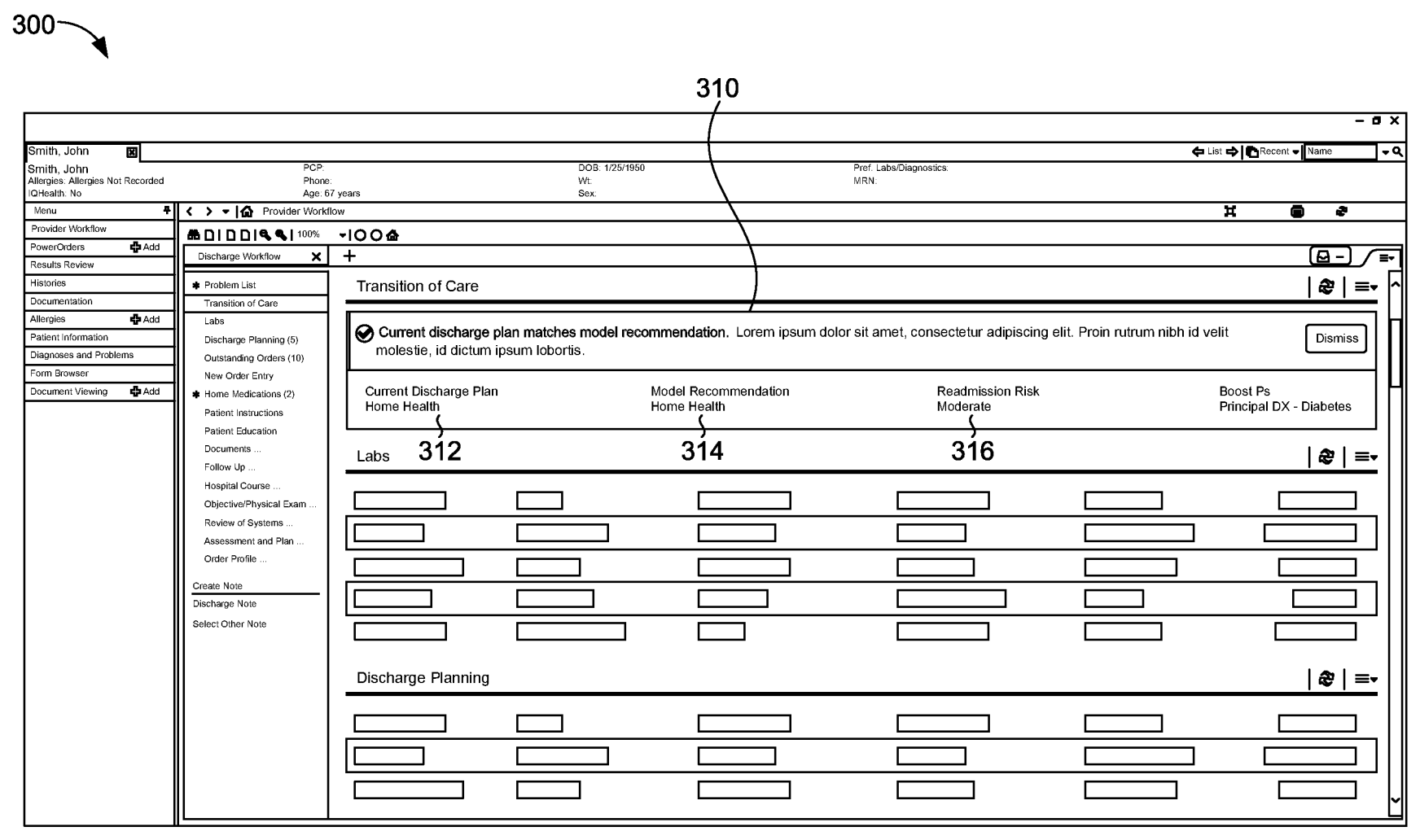

FIGS. 3-6 are illustrative screen displays showing workflow analytics in accordance with embodiments of the present invention;

FIG. 7 depicts a flow diagram of a method for providing workflow analytics, in accordance with an embodiment of the present invention; and FIG. 8 is a flow diagram of a method for training a workflow analytics system, in accordance with embodiments of the invention.

DETAILED DESCRIPTION

Figure 1:
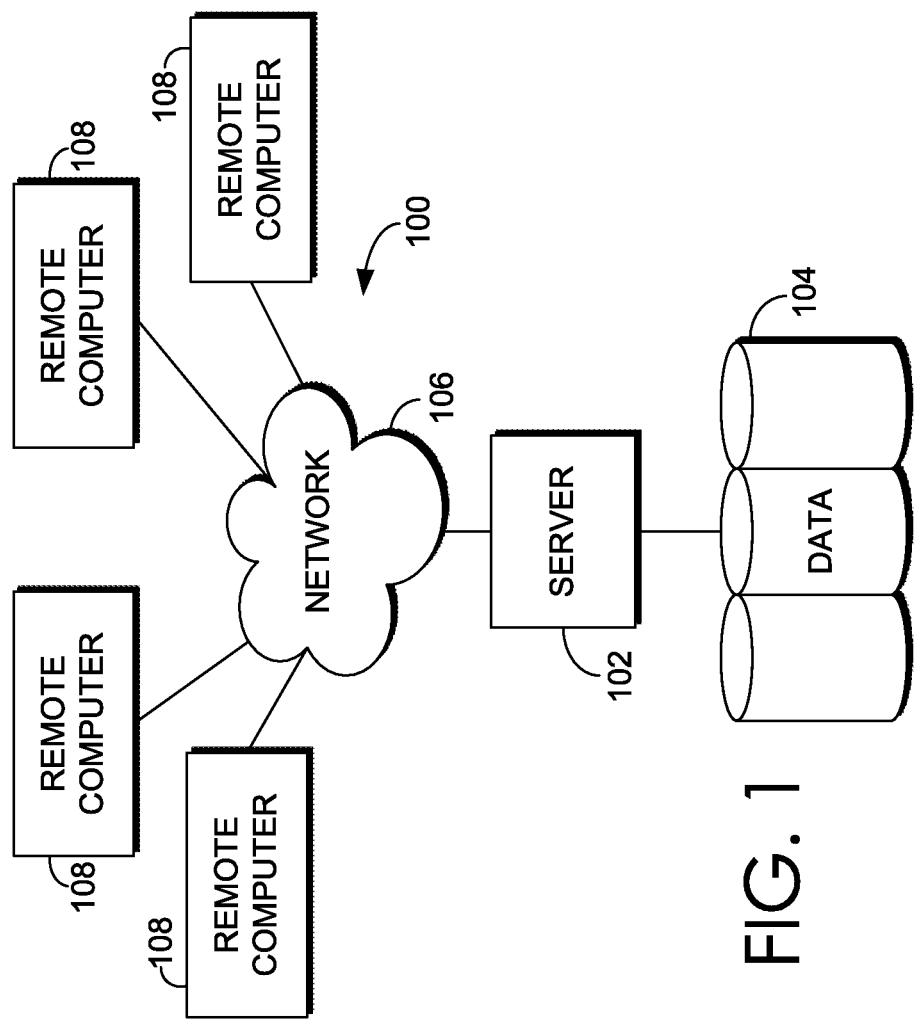
FIG. 1 is a block diagram of an exemplary operating environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the background, the modern practice of medicine poses a number of challenges for clinicians to effectively deliver quality care to patients. In particular, the effective medical knowledge base continues to grow at a rapid pace, making it difficult for clinicians to keep up with and carry out recognized best practices. For instance, thousands of new journal articles are published each month providing a plethora of new evidence-based clinical information. Additionally, new drugs, treatment techniques, and testing procedures are continuously being researched and developed. The difficulty for clinicians to keep appraised of such information is exacerbated by the fact that clinicians are typically pulled in many different directions by a vast number of patients. Moreover, clinicians must often make quick decisions regarding patient treatment. Information that is readily available is provided in general terms, without the benefit of analytics. This lack of analytics within the workflow prevents the clinician from weighing the evidence-based clinical information within the actual workflow. As a result, there currently exists a gap between evidence-based information and actual clinician practices. This gap contributes to decreased quality of care, increased risk of medical errors, and increased cost of healthcare.

Embodiments of the present disclosure relate to integrating multi-source data (i.e., analytics) into the clinical decision workflow. Analytics relevant to a particular patient are provided within the clinical decision workflow to provide data-driven decision support. When information is received from an end user device at a workflow service that indicates characteristics of a clinical decision support workflow being managed by the end user device for a patient, data is requested from one or more knowledge systems and electronic health record (EHR) data is requested from one or more EHRs. The data and the EHR data is aggregated within the clinical decision support workflow and a recommendation is provided to a clinician at a point of care via the end user device. For example, the recommendation may reveal that a particular care plan is, according to the aggregated data, the model recommendation.

In some cases, the clinician may select a care plan that is not, according to the analytics data, the model recommendation. In either case, differences in costs, readmission risks, outcomes, claims data, and the like between different care plans (e.g., the selected care plan, the model recommendation, or other care plans) are provided that help the clinician readily assess a comprehensive overview of the available analytics.

In embodiments, the clinician is prompted to provide feedback when the recommendation is discarded in favor of another care plan. For example, if the clinician moves forward with another care plan, the clinician may provide reasons why the selection was made. This feedback may be utilized to train a workflow service to identify additional data relevant (based on the reasons provided by the clinician) to the care plan that may be curated by a human supervisor or automatically incorporated in future or additional recommendations. In this way, additional recommendations provided by the workflow service may include the additional data when considering similar workflows and/or similar patients.

Accordingly, one embodiment of the present disclosure is directed to a system for providing workflow analytics. The system comprises a processor; and a non-transitory computer storage medium storing computer-useable instructions that, when used by the processor, cause the processor to: receive, at a workflow service, information from an end user device, the information indicating characteristics of a clinical decision support workflow being managed by the end user device for a patient; based on the clinical decision support workflow, requesting data from one or more knowledge systems and electronic health record (EHR) data from one or more EHRs, the data including analytics, best practices, claims information, or clinical statistics; and aggregate the data and the EHR data within the clinical decision support workflow and provide a recommendation to a clinician at a point of care via the end user device.

In another embodiment, the present disclosure directed to a computerized method for providing workflow analytics. The method comprises receiving, at a workflow service, information from an end user device. The information indicates characteristics of a clinical decision support workflow being managed by the end user device for a patient. The method also comprises, based on the clinical decision support workflow, requesting data from one or more knowledge systems and one or more electronic health record (EHR) data from one or more EHRs. The data includes analytics, best practices, claims information, or clinical statistics. The method further comprises aggregating the data and the EHR data within the clinical decision support workflow and providing a recommendation to a clinician at a point of care via the end user device.

In yet another embodiment, the present disclosure is directed to one or more computer storage media having computer-executable instructions embodied thereon that, when executed by a computer, causes the computer to perform operations to train a workflow analytics system. The operations comprise prompting the clinician to provide feedback in accordance with a selection of a care plan that, based on an aggregation of data received from one or more knowledge systems and electronic health record (EHR) data received from one or more EHRs, is not a recommended care plan. The operations also comprise utilizing the feedback to train a workflow service to identify additional data relevant to the recommendation.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

In some embodiments, remote computers 108 comprise computing-devices that are part of a cloud-computing platform. In some embodiments, a remote computer 108 is associated with a health records, data source such as an electronic health record (EHR) system of a hospital or medical organization, a health information exchange EHR, insurance provider EHR, ambulatory clinic EHR, or patient-sensor, or other data source, and facilitates accessing data of the source and communicating the data to control server 102 and/or other computing devices on a cloud computing platform, including other remote computers 108.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
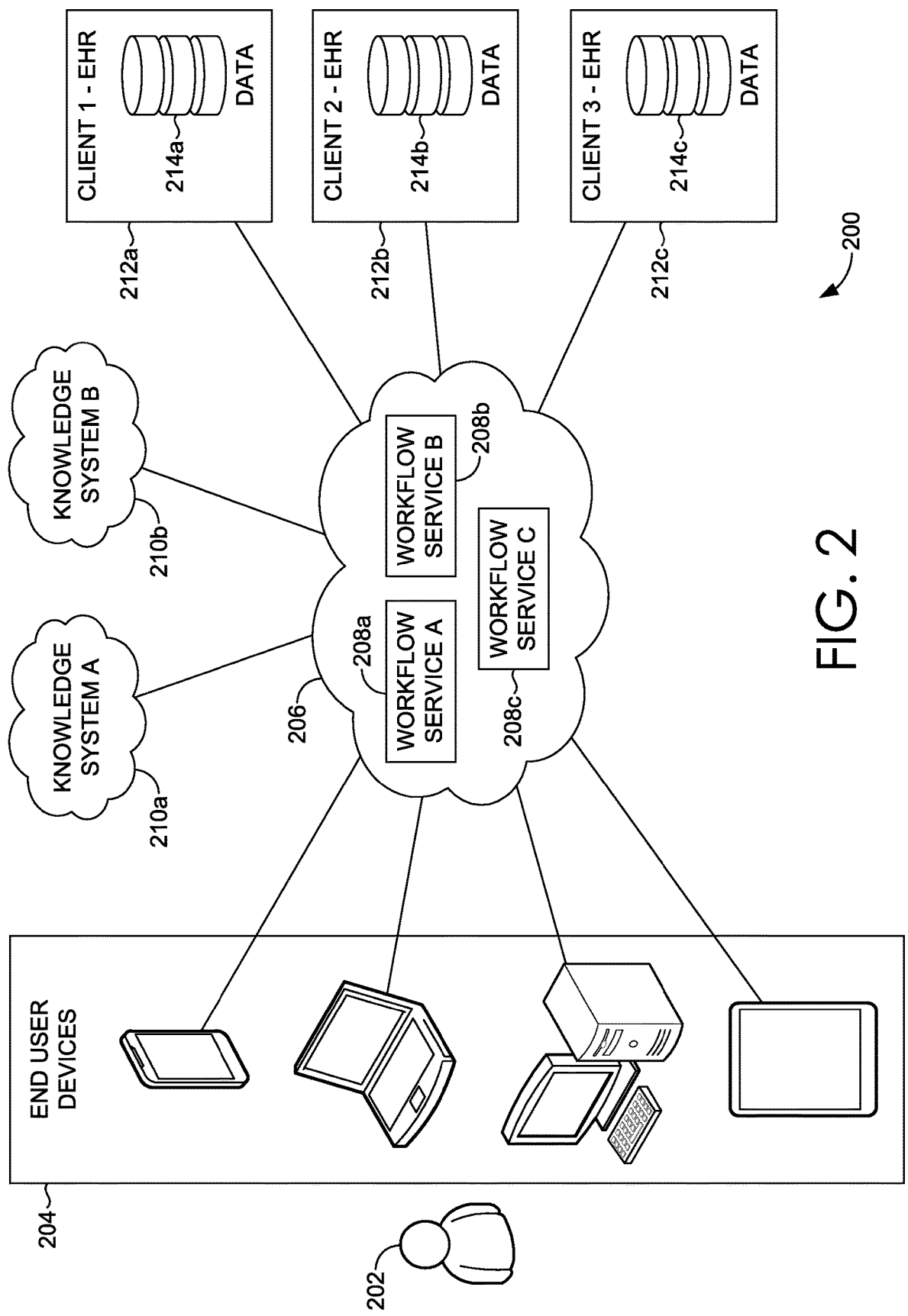
FIG. 2 a block diagram of an exemplary system including a workflow analytics system in accordance with an embodiment of the present invention.

Turning now to FIG. 2, an exemplary framework of a workflow analytics system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location.

Various functions described herein as being performed by one or more entities may be carried out by hardware, firmware, and/or software. For instance, various functions may be carried out by a processor executing instructions stored in memory. The workflow analytics system 200 may be implemented via any type of computing device, such as computing device 100 described above with reference to FIG. 1, for example.

The workflow analytics system 200 generally operates integrating multi-source data (i.e., knowledge systems) into the clinical decision workflow. For clarity, a knowledge system is a system outside of a particular EHR that is capable of analyzing broader trends and making suggestions. Knowledge systems may include claims data, outcomes data from within the healthcare facility or organization, third party outcomes data, best practices, analytics, and/or clinician feedback (e.g., collectively referred to as "data"). Data relevant to a particular patient is provided within the clinical decision workflow to provide data-driven decision support. When an indication from an end user device is received that indicates characteristics of a clinical decision support workflow being managed by the end user device for a patient, data is requested from one or more knowledge systems. EHR data that supports the workflow may also be requested from one or more EHRs.

The data may be derived from patients similar to the patient (e.g., similar demographics including similar conditions, diagnoses, treatments, ethnic backgrounds, socioeconomic backgrounds, genetics markers, age, gender, treating clinicians, or patients from a similar geographic region or being treated at similar healthcare facilities). The workflow analytics system 200 may be trained to identify which data is meaningful to various clinical decision workflows based on other data (e.g., selections made by a clinician or other data from a knowledge system or an EHR) corresponding to the patient. The data and the EHR data is aggregated within the clinical decision workflow and a recommendation is provided to a clinician at a point of care via the end user device.

As shown in FIG. 2, the workflow analytics system 200 includes, among other components not shown, end user device(s) 204, a workflow service 208, knowledge system A 210a, knowledge system B 210b, and data stores 212a, 212b, 212c. It should be understood that the workflow analytics system 200 shown in FIG. 2 is an example of one suitable computing system architecture. Each of the components shown in FIG. 2 may be implemented via any type of computing device, such as computing device 100 described with reference to FIG. 1, for example.

The components may communicate with each other via a network, which may include, without limitation, one or more local area networks (LANs) and/or wide area networks (WANs). Such networking environments are commonplace in offices, enterprise-wide computer networks, intranets, and the Internet. It should be understood that any number of comparison engines and clinical decision support engines may be employed within the workflow analytics system 200 within the scope of the present disclosure. Each may comprise a single device or multiple devices cooperating in a distributed environment. For instance, the workflow service may be provided via multiple devices arranged in a distributed environment that collectively provide the functionality described herein. In other embodiments, a single device may provide the functionality of multiple components of the workflow analytics system 200. For example, a single device may provide the knowledge system and the workflow service. In some embodiments, some or all functionality provided by the workflow service may be provided by a user device. Additionally, other components not shown may also be included within the network environment. As illustrated, the workflow service is provided as a cloud service.

Generally, the workflow service 208 provides analytics relevant to a particular patient within the clinical decision workflow to provide data-driven decision support. Different types of clinical decision support systems are available that may support various aspects of the clinical care process, such as clinical diagnosis and treatment planning, thereby advancing clinicians' use of best practices. In one form, current clinical decision support systems provide decision support through advice and alerts that are triggered based on stored clinical information. The primary source of clinical decision support is from commercially available sources, such as through products offered by First DataBank, Medispan, or Cerner Multum. The content of such sources is based on public literature and information from pharmaceutical manufacturers.

Each of knowledge system A 210a, knowledge system B 210b is configured to store information for use by, for example, workflow service 208. The information stored in association with the knowledge system A 210a and knowledge system B 210b is configured to be searchable for one or more items of information stored in association therewith. The information stored in association with the knowledge system A 210a and knowledge system B 210b may comprise evidence-based information (e.g., analytics) information used by the workflow service 208.

Additionally, knowledge system A 210a and knowledge system B 210b may store information concerning decision-support algorithms, reference materials, standards of care, recommendation protocols, alert protocols, and the like. This information may be specific to a healthcare facility, or the information may be promulgated by, for example, nationally-recognized medical organizations or governing bodies.

The content and volume of such information in the knowledge system A 210a and knowledge system B 210b is not intended to limit the scope of embodiments of the present invention in any way. Further, though illustrated as a plurality of independent components, the knowledge system A 210a and knowledge system B 210b may, in fact, be a plurality of database clusters, portions of which may reside on end user device(s) 204, in workflow service 208, on components not illustrated, and/or any combination thereof.

The data stores 212a, 212b, 212c may store EHRs of patients 214a, 214b, 214c associated with one or more healthcare facilities. EHRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

Upon receiving a call from an end user device 204, workflow service 208 determines specific characteristics of the workflow (e.g., workflow service A 208a, workflow service B 208b, or workflow service C 208c) being managed. To do so, specific information may be provided form the end user device such as user and/or patient identifiers.

Once the workflow service 208 determines the appropriate workflow, workflow service 208 integrates multi-source data (e.g., data stored in knowledge system A 210, knowledge system B 210 b, and/or data stores 212a, 212b, 212c) into the clinical decision workflow. For example, analytics relevant to a particular patient can be provided within the clinical decision workflow to provide data-driven decision support. This enables the clinician to determine how a recommended care plan compares to other care plans available to the patient. The comparison may be based on analytics, outcomes, claims data, and the like for patients similar to the particular patient.

End user device 204 may be any type of computing device used within a healthcare facility to receive, display, and send information to or from a component of a healthcare information system, such as a workflow service 208. End user device 204 may be capable of communicating via a network with workflow service 208, knowledge system A 210, knowledge system B 210 b, and/or datastores 212a, 212b, 212c. Such devices may include any type of mobile and portable devices including cellular telephones, personal digital assistants, tablet PCs, smart phones, and the like.

End user device 204 is configured to display information to a clinician via a display. The information may include communications initiated by and/or received by the workflow service 208. Embodiments are not intended to be limited to visual display but rather may also include audio presentation, visual presentation, combined audio/visual presentation, and the like.

As mentioned, the analytics data is derived from patients similar to the patient (e.g., similar demographics including similar conditions, diagnoses, treatments, ethnic backgrounds, socioeconomic backgrounds, genetics markers, age, gender, treating clinicians, or patients from a similar geographic region or being treated at similar healthcare facilities). As can be appreciated, any number or type of demographics may be utilized by the workflow service 208 and, as described below, the number or type of demographics utilized is dynamic and may be learned based on feedback provided by a clinician.

Data received from knowledge system A 210, knowledge system B 210 b, and/or data stores 212a, 212b, 212c is aggregated and a recommendation is provided within the clinical decision support workflow to a clinician at a point of care. It is up to the clinician to determine whether the model recommendation is appropriate as the care plan for the patient. Supporting data or visuals may be provided within the workflow by the workflow service to assist the clinician in making the determination.

The recommendation may reveal additional data about the selected care plan, the model recommendation, or other care plans. For example, the recommendation may reveal costs corresponding to each care plan available to the patient that may help the clinician determine the most cost-effective plan. The recommendation may additionally reveal readmission risks corresponding to each care plan available to the patient that may help the clinician to appropriately convey any readmission risks to the patient.

In embodiments, the clinician is prompted to provide feedback in accordance with a selection of the care plan other than the model recommendation. For example, if the clinician moves forward with a care plan, even though it is not the model recommendation, the clinician may provide reasons why the selection was made. This feedback may be utilized to train the workflow service 208 to identify additional data relevant (based on the reasons provided by the clinician) to the care plan. The workflow service may include or consider the additional data in additional or future recommendations for a particular workflow when used for other patients. For example, the clinician may provide feedback indicating that the patient has a particular demographic that may make one care plan more appropriate than another. The workflow service 208 utilizes this feedback to consider the particular demographic when providing additional recommendations.

In other embodiments, the workflow service 208 may provide a recommendation in addition to demographics that were considered relevant to the recommendation. If the clinician disagrees, and provides feedback indicating which demographics are not relevant to particular patient, the workflow service 208 may utilize this feedback such that it no longer considers the particular demographic when providing additional recommendations for that particular workflow.

In both cases, whether the clinician disagrees with a demographic that was considered or believes another demographic should have been considered, even if the feedback is not explicit, the workflow service 208 may infer such information based on the feedback that is provided. In addition, the feedback may not be used in such an absolute fashion by the workflow service 208. As can be appreciated, clinicians may not agree when with one another in selecting care plans or providing feedback. Thus, the workflow service 208 may provide weight to the feedback so that a demographic may be considered more or less based on aggregate feedback, as compared to other demographics being considered, but not necessarily completely removed or wholly added.

The workflow service 208 may utilize one or more machine learning algorithms to determine the data that should be considered for a particular workflow as well as the model recommendation. For example, an ensemble of alternating decision trees can be used to determine, based on available data, the most effective care plan (i.e., the model recommendation) for the patient. In another example, an ensemble of alternating decision trees can be used to determine, based on information received from the end user device 204, which workflow service (workflow service A 208a, workflow service B 208b, or workflow service C 208c) should be utilized. In yet another example, an ensemble of alternating decision trees can be used to determine, based on the workflow being provided, which data should be utilized to provide the model recommendation. Each decision tree may be trained on a random subset of instances and features of the healthcare data. In some embodiments, the number of decision trees used is based on the type of healthcare data received or specific information pertaining to the patient.

A generic decision tree is a decision support tool that arrives at a decision after following steps or rules along a tree-like path. While most decision trees are only concerned about the final destination along the decision path, alternating decision trees take into account every decision made along the path and may assign a score for every decision encountered. Once the decision path ends, the algorithm sum all of the incurred scores to determine a final classification (i.e., the model recommendation). In some embodiments, the alternating decision tree algorithm may be further customized. For example, the alternating decision tree algorithm may be modified by wrapping it in other algorithms.

A machine learning algorithm may use a generic cost matrix. The intuition behind the cost matrix is as follows. If the model predicts a member to be classified in group A, and the member really should be in group A, no penalty is assigned. However, if this same member is predicted to be in group B, C, or D, a 1-point penalty will be assigned to the model for this misclassification, regardless of which group the member was predicted to be in. Thus, all misclassifications are penalized equally. However, by adjusting the cost matrix, penalties for specific misclassifications can be assigned. For example, where someone who was truly in group D was classified in group A, the model could increase the penalty in that section of the cost matrix. A cost matrix such as this may be adjusted as needed to help fine tune the model for different iterations, and may be based on the specific patient in some embodiments.

With regards to a multi-class classifier, some machine learning algorithms, such as alternating decision trees, generally only allow for the classification into two categories (e.g. a binary classification). In cases where it is desired to classify three or more categories, a multi-class classifier is used.

In order to assist the alternating decision tree in selecting best features for predictive modeling, an ensemble method called rotation forest may be used. The rotation forest algorithm randomly splits the dataset into a specified number of subsets and uses a clustering method called Principal Component Analysis to group features deemed useful. Each tree is then gathered (i.e., "bundled into a forest") and evaluated to determine the features to be used by the base classifier.

Various alternative classifiers may be used to provide the workflow analytics. Indeed, there are thousands of machine learning algorithms, which could be used in place of, or in conjunction with, the alternating decision tree algorithm. For example, one set of alternative classifiers comprise ensemble methods.

Ensemble methods use multiple, and usually random, variations of learning algorithms to strengthen classification performance. Two of the most common ensemble methods are bagging and boosting. Bagging methods, short for "bootstrap aggregating" methods, develop multiple models from random subsets of features from the data ("bootstrapping"), assigns equal weight to each feature, and selects the best-performing attributes for the base classifier using the aggregated results. Boosting, on the other hand, learns from the data by incrementally building a model, thereby attempting to correct misclassifications from previous boosting iterations.

Regression models are frequently used to evaluate the relationship between different features in supervised learning, especially when trying to predict a value rather than a classification. However, regression methods are also used with other methods to develop regression trees. Some algorithms combine both classification and regression methods; algorithms that used both methods are often referred to as CART (Classification and Regression Trees) algorithms.

Bayesian statistical methods are used when the probability of some events happening are, in part, conditional to other circumstances occurring. When the exact probability of such events is not known, maximum likelihood methods are used to estimate the probability distributions. A textbook example of Bayesian learning is using weather conditions, and whether a sprinkler system has recently gone off, to determine whether a lawn will be wet. However, whether a homeowner will turn on their sprinkler system is influenced, in part, to the weather. Bayesian learning methods, then, build predictive models based on calculated prior probability distributions.

Another type of classifiers comprise artificial neural networks. While typical machine learning algorithms have a pre-determined starting node and organized decision paths, the structure of artificial neural networks are less structured. These algorithms of interconnected nodes are inspired by the neural paths of the brain. In particular, neural network methods are very effective in solving difficult machine learning tasks. Much of the computation occurs in "hidden" layers.

By way of example and not limitation, other classifiers and methods that may be utilized include (1) decision tree classifiers, such as: C4.5—a decision tree that first selects features by evaluating how relevant each attribute is, then using these attributes in the decision path development; Decision Stump—a decision tree that classifies two categories based on a single feature (think of a single swing of an axe); by itself, the decision stump is not very useful, but becomes more so paired with ensemble methods; LADTree—a multi-class alternating decision tree using a LogitBoost ensemble method; Logistic Model Tree (LMT)—a decision tree with logistic regression functions at the leaves; Naive Bayes Tree (NBTree)—a decision tree with naive Bayes classifiers at the leaves; Random Tree—a decision tree that considers a pre-determined number of randomly chosen attributes at each node of the decision tree; Random Forest—an ensemble of Random Trees; and Reduced-Error Pruning Tree (REPTree)—a fast decision tree learning that builds trees based on information gain, then prunes the tree using reduce-error pruning methods; (2) ensemble methods such as: AdaBoostMl—an adaptive boosting method; Bagging—develops models using bootstrapped random samples, then aggregates the results and votes for the most meaningful features to use in the base classifier; LogitBoost—a boosting method that uses additive logistic regression to develop the ensemble; MultiBoostAB—an advancement of the AdaBoost method; and Stacking—a method similar to boosting for evaluating several models at the same time; (3) regression methods, such as Logistic Regression—regression method for predicting classification; (4) Bayesian networks, such as BayesNet—Bayesian classification; and NaiveBayes—Bayesian classification with strong independence assumptions; and (4) artificial neural networks such as MultiLayerPerception—a forward-based artificial neural network.

In practice, and still referring to FIG. 2, a user 202 (e.g., clinician, administrator, patient, care team member, etc.) invokes a workflow with the scope supporting the user's role. For example, a workflow may focus on a particular patient for a clinician user (e.g., statistical information on the efficiency of a nurse unit for a charge nurse or administrator). The end user device 204 invokes a call to a workflow service (e.g., workflow service A 208*a*, workflow service B 208*b*, or workflow service C 208*c*).

The workflow service is provided specific information from the end user device 204 to indicate the specific characteristics of the workflow being managed. The exact details provided may vary based on the workflow being supported. For example, a clinical workflow may pass through the user and patient identifiers as part of interacting with a particular patient.

The workflow service invokes a Business to Business (B2B) connection to one of multiple analytics or knowledge systems (e.g., knowledge system A 210*a*, knowledge system B 210*b*), based on the workflow being supported, to pass along standardized identifications to specific external providers. The mechanism for authorizing, sharing, and securing information in transit between systems is supported by two different mechanisms depending on the form of the data returned by the knowledge systems.

For simple transactions involving structured data (e.g., JSON, XML, etc.), a JSON web token or OAUTH token is used to pass the appropriate authentication and scope of access information between the different systems. For transactions involving complex rendering (e.g., retrieving a component rendered by HTML and JAVASCRIPT that internally makes multiple AJAX calls as part of the display process), a session is generated during the authorization process that allows a secure cookie to be included in the initial response from the workflow service to the user device 204. Subsequent calls to load additional information will automatically leverage this secure cookie in order to obtain additional data as needed.

Prior to any workflows being triggered, a trust relationship is configured between the workflow service and all of the knowledge systems. This allows a user already authenticated on an EHR system, which is supported by the workflow service, to make use of the analytics and knowledge information without any additional user interaction. The knowledge systems leverage the standardized IDs to generate and return broader analytics and recommendation information based on curated information involving best practices, claims information, clinical statistics, etc.

The centralized component aggregates, normalizes, and performs business processing on the information from the knowledge systems and the EHR. The information obtained from the EHR originates from the appropriate database (e.g., client 1—EHR 212*a*, client 2—EHR 212 *b*, client 3—EHR, 212 *c*) for a given workflow concept. The user device 204 receives the combined output of the EHR information as well as the recommendation information to be rendered.

The end user 202 may review the workflow and recommendation information and document the specific action(s) to be taken. Providing this knowledge-based information within the end user's existing workflow is the key to improving the health and business outcomes based on the challenges described herein. An end user 202 is empowered to make more informed decisions without having to delay actions otherwise necessary (e.g., patient care). If the end user 202 overrides the recommendation information, that data along with any appropriate contextual information may be communicated back to all appropriate knowledge systems. The data from end user overrides is reviewed on a continual basis so that updates can be made to the underlying algorithms and datasets that are the foundation of the recommendation provided by the knowledge systems, resulting in more accurate future recommendations.

Referring now to FIGS. 3-6, illustrative screen displays 300, 400, 500, 600 show workflow analytics in accordance with embodiments of the present invention. Initially, FIG. 3. illustrates a recommendation 310 within the clinical decision support workflow. As illustrated, the recommendation 310 indicates that the current care plan (e.g., a discharge plan) matches the model recommendation. Additionally, the recommendation identifies the current discharge plan 312, the model recommendation 314, and the readmission risk 316.

Figure 4:
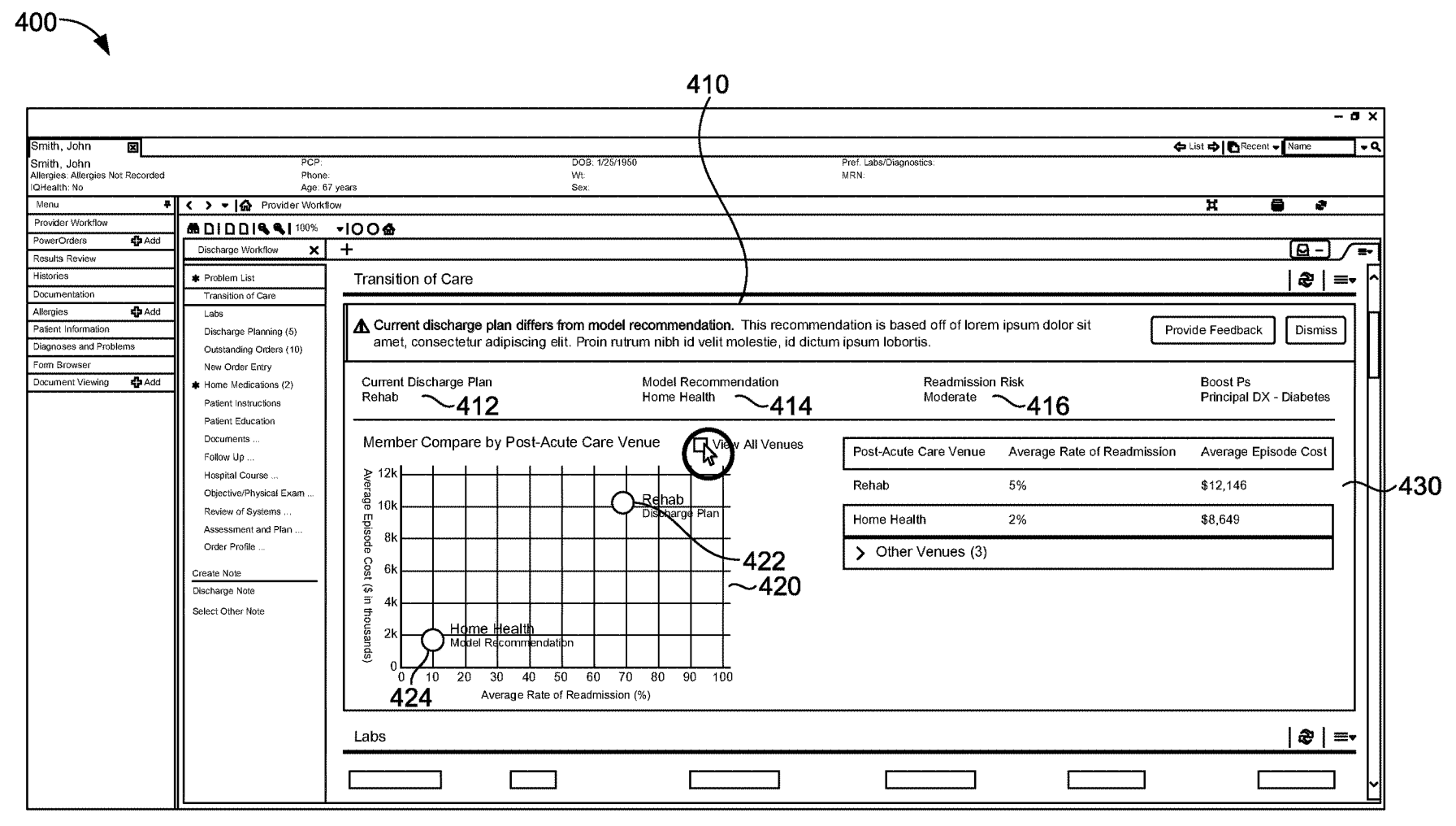

FIG. 4. illustrates a recommendation 410 within the clinical decision support workflow. As illustrated, the recommendation 410 indicates that the current care plan (e.g., a discharge plan) differs from the model recommendation. Additionally, the recommendation identifies the current discharge plan 412, the model recommendation 414, and the readmission risk 416. A graphical comparison 420 is also provided that illustrates cost versus readmission risk for the current discharge plan 422 and the model recommendation 424. The recommendation further identifies, in a chart 430, the average rate of readmission and the average episode cost for the current discharge plan and the model recommendation.

Figure 5:
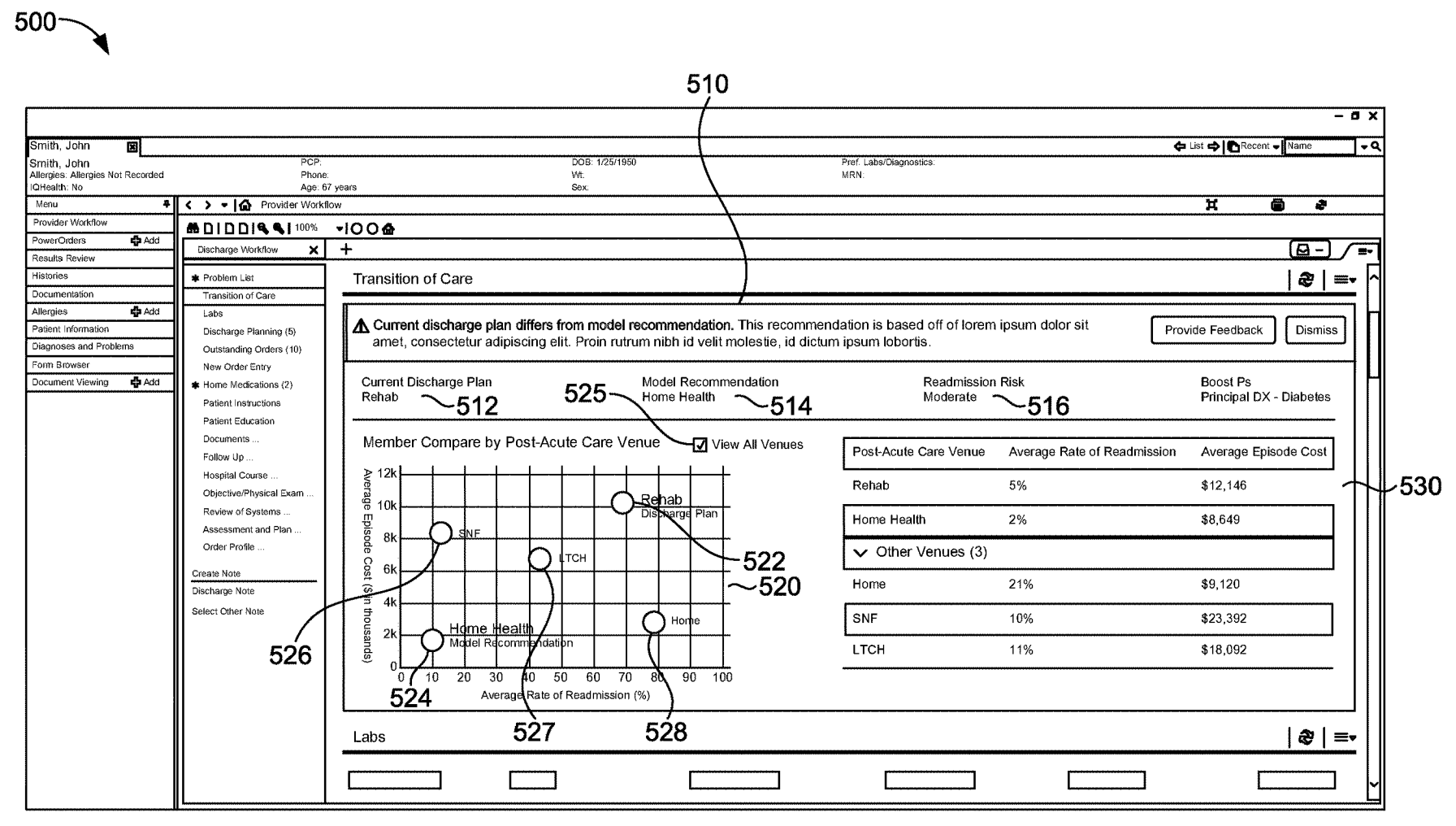

In FIG. 5, a recommendation 510 is illustrated within the clinical decision support workflow. As illustrated, the recommendation 510 indicates that the current care plan (e.g., a discharge plan) differs from the model recommendation. Additionally, the recommendation identifies the current discharge plan 512, the model recommendation 514, and the readmission risk 516. This time, a selection 525 was made to view a graphical comparison 520 for all venues. Again, the graphical comparison 520 illustrates cost versus readmission risk for the current discharge plan 522, the model recommendation 524, and other available care plans 526, 527, 528. The recommendation further identifies, in a chart 530, the average rate of readmission and the average episode cost for the current discharge plan, the model recommendation, and other available care plans.

Figure 6:
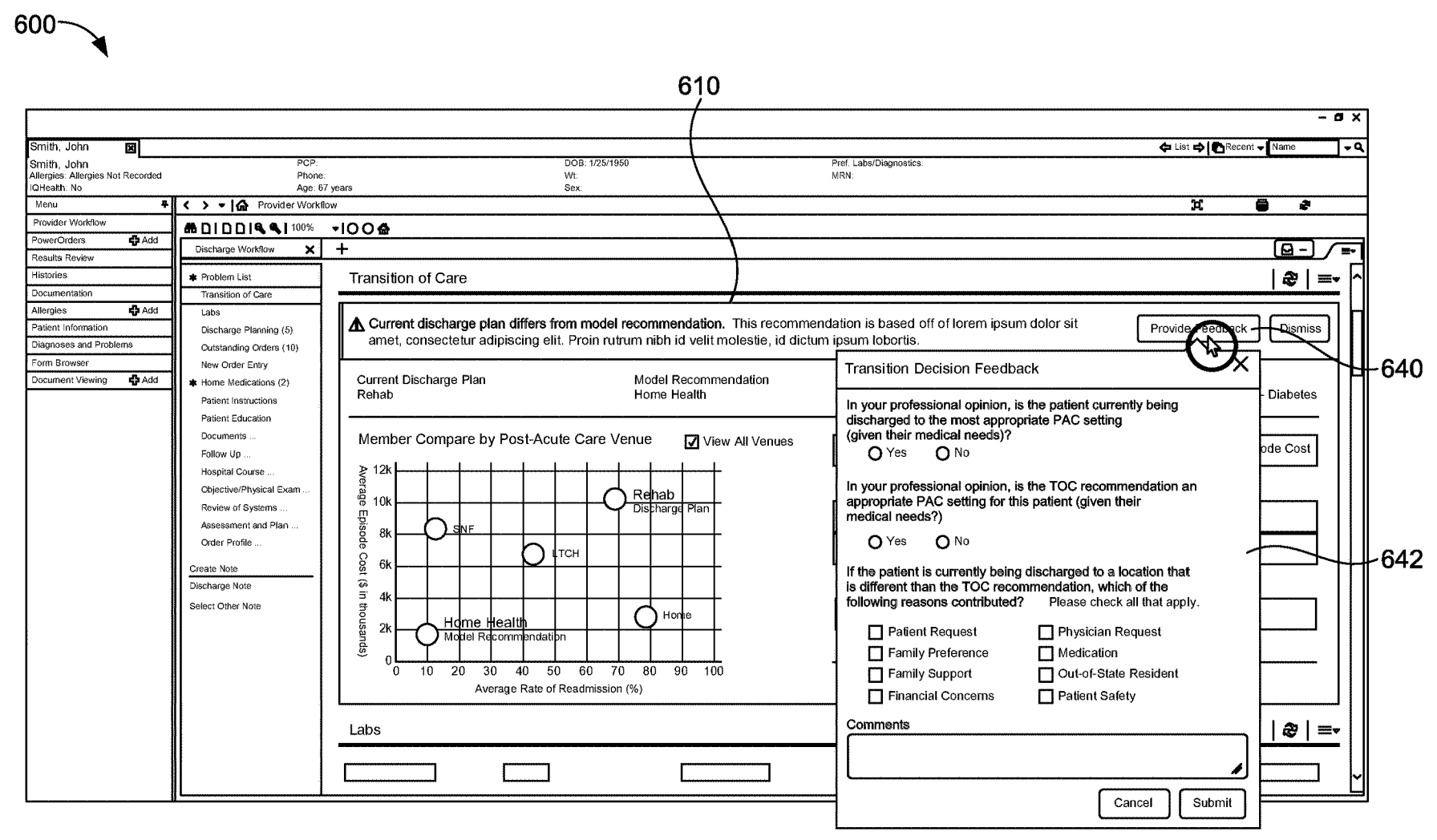

Referring next to FIG. 6, a recommendation 610 is illustrated within the clinical decision support workflow. As illustrated, the recommendation 610 indicates that the current care plan (e.g., a discharge plan) differs from the model recommendation. Because the current care plan differs from the model recommendation, the clinician is prompted to provide feedback 640. A feedback area 642 enables the clinician to answer questions indicating why the clinician has selected a care plan that differs from the model recommendation. This feedback may be utilized, such as by a workflow service and/or knowledge system, to identify factors that may provide more accurate analytics in additional recommendations for similar patients.

Turning now to FIG. 7, a flow diagram is provided illustrating a method 700 for providing workflow analytics, in accordance with embodiments of the present invention. Method 700 may be performed by any computing device (such as computing device described with respect to FIG. 1) with access to a workflow analytics system (such as the one described with respect to FIG. 2) or by one or more components of the workflow analytics system.

Initially, at step 710, information from an end user device is received at a workflow service. The information indicates characteristics of a clinical decision support workflow being managed by the end user devices for a patient. For example, the characteristics may indicate that a particular patient with a particular condition may be ready for discharge. The workflow service may identify several discharge plans. For instance, the discharge plan may be to discharge the patient to a post-acute care venue. Alternatively, the discharge plan may be to discharge the patient to home health model, a skilled nursing facility, or a long term acute care hospital.

At step 720, based on the clinical decision support workflow, data is requested from one or more knowledge systems and HER data is requested from one or more EHRs. The data includes analytics, best practices, claims information, or clinical statistics. The data may be derived from patients similar to the patient. For example, analytics may indicate one care plan has different outcomes for different types of patients (based on demographic data provided by the end user device or EHR). In this way, only analytics from patients similar to the patient may be used to provide recommendations.

At step 730, the data and the EHR data is aggregated within the clinical decision support workflow and a recommendation is provided to a clinician at a point of care via the end user device. In embodiments, the recommendation is provided without requiring the clinician to initiate access to software other than the clinical decision support workflow. This enables the clinician to realize the benefit of analytics data at the point of care.

Turning now to FIG. 8, a flow diagram is provided illustrating a method 800 for training a workflow analytics system, in accordance with embodiments of the present invention. Method 800 may be performed by any computing device (such as computing device described with respect to FIG. 1) with access to a workflow analytics system (such as the one described with respect to FIG. 2) or by one or more components of the workflow analytics system.

Initially, at step 810, a clinician is prompted to provide feedback in accordance with a selection of the care plan that, based on an aggregation of data received from one or more knowledge systems and EHR data received from one or more EHRs, is not a recommended care plan. For example, if the clinician chooses to proceed with a care plan despite the analytics data suggesting other care plans might be more effective, the clinician is prompted to provide feedback to explain why the more effective care plans that were suggested were not selected. In some cases, certain factors relevant to the particular patient may not have been considered by a workflow analytics system. Such consideration might otherwise affect the model recommendation or the effectiveness of other care plans.

At step 820, the feedback is utilized to train a workflow service to identify additional data (e.g., the particular demographic data) relevant to the care plan. In this way, if a clinician determines that data not being considered by the workflow service affects what care plan should be recommended, the clinician can provide such feedback as described above, which can be utilized to train the workflow service. Alternatively, a human supervisor may curate the feedback to identify additional data relevant (based on the reasons provided by the clinician) to the recommendation that can be incorporated in future or additional recommendations.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A system for providing workflow analytics, the system comprising:
   a processor; and
   a non-transitory computer storage medium storing computer-useable instructions that, when used by the processor, cause the processor to:
   provide, by a workflow service a clinical decision support workflow for a patient to an end user device;

based on the provided clinical decision support workflow, requesting, by the workflow service, data from one or more knowledge systems, the data including analytics, claims information, or clinical statistics;

provide the data, by the workflow service, within the clinical decision support workflow and provide a recommendation to a clinician at a point of care via the end user device, the recommendation based on the data, comprising a care plan for the patient, and indicating readmission risk for the care plan;

upon the clinician not selecting the care plan, further comprising prompting the clinician to provide feedback to the workflow service via the end user device;

based on the feedback, inferring additional data relevant to the clinical decision workflow; and training the workflow service to consider the additional data in future recommendations for the clinical decision workflow.

2. The system of claim 1, further comprising including the additional data in additional recommendations.

3. The system of claim 1, wherein the clinical decision support workflow is a discharge plan.

4. The system of claim 1, wherein the analytics data is for a venue where the patient is currently being treated.

5. The system of claim 1, wherein the analytics data is for venues similar to a venue where the patient is currently being treated.

6. The system of claim 1, wherein the workflow service leverages access to third party resources.

7. The system of claim 1, wherein the recommendation is provided without requiring the clinician to initiate access to software other than the clinical decision support workflow.

8. A computerized method for providing workflow analytics, the method comprising:

receiving, at a workflow service, information from an end user device, the information indicating characteristics of a clinical decision support workflow being managed by the end user device for a patient;

based on the clinical decision support workflow, requesting data from one or more knowledge systems and electronic health record (EHR) data from one or more EHRs, the data including analytics, claims information, or clinical statistics;

present the data and the EHR data within the clinical decision support workflow and provide a recommendation to a clinician at a point of care via the end user device, the recommendation based on the data, comprising a care plan for the patient, and indicating whether the care plan is a model recommendation or readmission risk for the care plan;

upon the clinician not selecting the care plan, prompting the clinician to provide feedback to the workflow service via the end user device;

based on the feedback, inferring additional data relevant to the clinical decision workflow; and training the workflow service to consider the additional data in future recommendations for the clinical decision workflow.

9. The computerized method of claim 8, further comprising including the additional data in additional recommendations.

10. The computerized method of claim 8, wherein the clinical decision support workflow is a discharge plan.

11. The computerized method of claim 8, wherein the recommendation is provided without requiring the clinician to initiate access to software other than the clinical decision support workflow.

12. One or more computer storage media having computer-executable instructions embodied thereon that, when executed by a computer, causes the computer to perform operations to train a workflow analytics system, the operations comprising:

prompting the clinician to provide feedback in accordance with a selection of a care plan that, based on presenting data within a clinical decision workflow, the data comprising analytics or clinical statistics received from one or more knowledge systems, indicates the selection of the care plan is not a recommended care plan;

based on the feedback, inferring additional data relevant to the clinical decision workflow; and training the workflow service to consider the additional data in future recommendations for the clinical decision workflow.

13. The media of claim 12, further comprising receiving, at a workflow service, information from an end user device, the information indicating characteristics of a clinical decision support workflow being managed by the end user device for a patient.

14. The media of claim 12, further comprising presenting the data and the EHR data within the clinical decision support workflow and providing a recommendation to a clinician at a point of care via the end user device, the recommendation indicating whether a care plan is a model recommendation, costs corresponding to various care plans, or readmission risks for various plans.

15. The media of claim 12, wherein the clinical decision support workflow is a discharge plan.

* * * * *